(12) United States Patent
Snyder, III (10) Patent No.: US 8,454,901 B1
(45) Date of Patent: Jun. 4, 2013

(54) MOBILE APPARATUS AND METHOD TO STERILIZE SURGICAL TRAYS

(76) Inventor: Clarence J. Snyder, III, Sudlersville, MD (US)

( * ) Notice: Subject to any disclaimer, the term of this patent is extended or adjusted under 35 U.S.C. 154(b) by 79 days.

(21) Appl. No.: 12/387,673

(22) Filed: May 6, 2009

(51) Int. Cl.
*A61L 2/07* (2006.01)
(52) U.S. Cl.
USPC .......................................... 422/297; 422/26
(58) Field of Classification Search
USPC ................................................ 422/297, 26
See application file for complete search history.

(56) References Cited

U.S. PATENT DOCUMENTS

| | | | |
|---|---|---|---|
| 4,105,407 A | 8/1978 | Sanderson | |
| 4,626,971 A | 12/1986 | Schultz | |
| 4,643,303 A | 2/1987 | Arp et al. | |
| 4,762,688 A | 8/1988 | Berry, Jr. | |
| 5,281,400 A | 1/1994 | Berry, Jr. | |
| 5,369,892 A * | 12/1994 | Dhaemers | 34/275 |
| 5,415,846 A | 5/1995 | Berry, Jr. | |
| 5,535,141 A | 7/1996 | Lussi | |
| 5,588,623 A | 12/1996 | Leduc | |
| 5,843,388 A | 12/1998 | Arroyo et al. | |
| 5,893,618 A | 4/1999 | Lepage, Jr. | |
| 5,923,432 A * | 7/1999 | Kral | 356/432 |
| 6,073,547 A * | 6/2000 | Westbrooks et al. | 99/468 |
| 6,218,796 B1 * | 4/2001 | Kozlowski | 318/280 |
| 6,319,479 B1 * | 11/2001 | Houston | 422/292 |
| 6,926,874 B2 | 8/2005 | Ongaro | |
| 7,214,354 B2 | 5/2007 | Ongaro | |
| 7,544,915 B2 * | 6/2009 | Hu | 219/387 |
| 2003/0116636 A1 * | 6/2003 | Burkett et al. | 236/44 A |
| 2004/0096355 A1 | 5/2004 | Ishibiki | |
| 2004/0101456 A1 * | 5/2004 | Kuroshima et al. | 422/297 |
| 2005/0153052 A1 * | 7/2005 | Williams et al. | 426/634 |
| 2006/0032770 A1 | 2/2006 | Orbay et al. | |
| 2006/0108757 A1 * | 5/2006 | Brookmire et al. | 280/47.34 |
| 2007/0039294 A1 * | 2/2007 | Airey | 55/385.2 |
| 2007/0160494 A1 | 7/2007 | Sands | |
| 2008/0063580 A1 | 3/2008 | von Lersner | |
| 2008/0087231 A1 * | 4/2008 | Gabriel et al. | 119/455 |
| 2008/0172295 A1 * | 7/2008 | Watson | 705/14 |

* cited by examiner

*Primary Examiner* — Sean E Conley
(74) *Attorney, Agent, or Firm* — Sidney W. Kilgore, P.A.; Sidney W. Kilgore (57) ABSTRACT

A mobile apparatus and method to sterilize surgical trays. A cabinet has filtered cabinet roof vents, filtered cabinet floor vents, door(s) sealably covering a cabinet front aperture, shelves sized to support surgical trays, and wheels. Surgical trays are placed within the cabinet, the cabinet doors are closed, and the mobile apparatus is placed within an autoclave and sterilized. The cabinet doors are not unsealed until the cabinet is in the operating room, ready for use. During use in the operating room, doors are opened, trays removed, and their contents used. Wheels on the cabinet facilitate moving the cabinet from autoclave to storage or operating room. Chemical indicators and a locator card may be used to verify the sterilization status and autoclave history of the cabinet and its contents. Method steps include periodically replacing the filters and door gasket.

14 Claims, 12 Drawing Sheets

MOBILE APPARATUS AND METHOD TO STERILIZE SURGICAL TRAYS

BACKGROUND OF THE INVENTION

This invention relates to operating room sterilization equipment and methods, and in particular to a mobile apparatus and method to sterilize surgical trays.

A variety of instruments and supplies are required during modern operations. These are typically stored and sterilized in covered trays. For example, an average knee replacement operation requires approximately twelve trays containing the instruments and supplies needed for this operation.

Current sterilization procedures involve the steps of washing the trays individually, loading instruments and supplies into the tray, and then wrapping each tray individually with a protective wrap, frequently a 54 inch×54 inch sterile blue wrap. If the tray has sharp corners or protuberances, these must be padded with a towel to avoid tearing the protective wrap. The loaded trays are then placed on a cart and the cart inserted into a sterilization autoclave.

Within the autoclave, the cart loaded with trays is generally sterilized at 276 degrees Fahrenheit for thirty minutes and then removed from the autoclave. The trays must then be allowed to dry for an additional fifteen minutes before handling.

The cart bearing the trays is then taken into the operating room. During the course of the operation, each tray is inspected and unwrapped as its contents are needed for the procedure being performed. Each tray bears a chemical indicator which reads the sterilization status of the tray. Each chemical indicator must also be inspected.

It takes in the vicinity of eight minutes to inspect each tray and its chemical indicator and to unwrap the tray. Sterile 54 inch×54 inch wraps cost approximately $3, so a cart bearing twelve trays requires $3×12=$36 in sterile wraps. In addition, the cost of twelve chemical indicators must be added to the sterilization costs for the cart.

If a wrap is found to be torn or breached, the contents of the tray it embraces must be considered non-sterile. In such an event, the autoclaving procedure must be repeated (which takes about 45 minutes) or, in the alternative, an emergency "flash autoclave" may be performed. A flash autoclave involves sterilizing the tray in an autoclave for about ten minutes. A flash autoclave is not as thorough a sterilization as the full procedure and carries greater risks. Therefore, when a sterile wrap is discovered to be torn or breached in the operating room while a procedure is underway, the surgeon is faced with the choice of waiting 45 minutes for a full autoclave sterilization or ordering a flash autoclave if such delay is unacceptable. Any delay is potentially damaging to the patient, because time spent under anesthesia is best minimized.

Thus, it would be desirable to provide a mobile apparatus and method to sterilize surgical trays which does not require the use of protective wraps and which reduces the number of chemical indicators required. It would be additionally desirable to provide mobility to the apparatus to facilitate its introduction into an autoclave and to facilitate its transportation from the autoclave after sterilization to a storage area or the operating room.

SUMMARY OF THE INVENTION

Accordingly, it is an object of the present invention to provide a mobile apparatus and method to sterilize surgical trays which avoids having to wrap surgical trays with protective wrap. The mobile apparatus includes a cabinet into which surgical trays may be placed for sterilization until use. Advantages associated with the accomplishment of this object include elimination of the cost of purchasing protective wraps and reduced work associated with wrapping and unwrapping surgical trays.

It is another object of the present invention to provide a mobile apparatus and method to sterilize surgical trays which reduces the number of chemical indicators required. The mobile apparatus includes a cabinet into which surgical trays may be placed for sterilization until use and a number of chemical indicators placed in different locations within the cabinet. Benefits associated with the accomplishment of this object include reduced cost in chemical indicators and reduced labor inspecting chemical indicators.

It is still another object of this invention to provide a mobile apparatus and method to sterilize surgical trays which is easily moved. The mobile apparatus includes wheels attached to the floor of the cabinet. An advantage associated with the realization of this object is reduced labor introducing the mobile apparatus to sterilize surgical trays into an autoclave and reduced effort moving the mobile apparatus into a storage area or operating room.

It is another object of the present invention to provide a mobile apparatus and method to sterilize surgical trays which avoids the time delay associated with torn or breached protective wrap around sterilized surgical trays. The mobile apparatus includes a cabinet into which surgical trays may be placed for sterilization until use. A benefit associated with the accomplishment of this object is elimination of the delay associated with re-sterilization of a surgical tray whose protective wrap is found to be torn or breached and reduction in patient risk associated with such delay, causing increased patient time under anesthesia.

BRIEF DESCRIPTION OF THE DRAWINGS

The invention, together with the other objects, features, aspects and advantages thereof will be more clearly understood from the following in conjunction with the accompanying drawings.

DETAILED DESCRIPTION OF THE INVENTION

The invention comprises cabinet 2 with shelves 70 capable of admitting at least one surgical tray 80. After at least one surgical tray 80 is loaded into cabinet 2, and then cabinet 2 is inserted into an autoclave and sterilized. Then cabinet 2 is rolled on wheels 104 into storage or directly into an operating room where its surgical tray(s) 80 are removed and used as required, thus avoiding the necessity of protective wraps and redundant chemical indicators.

Figure 1:
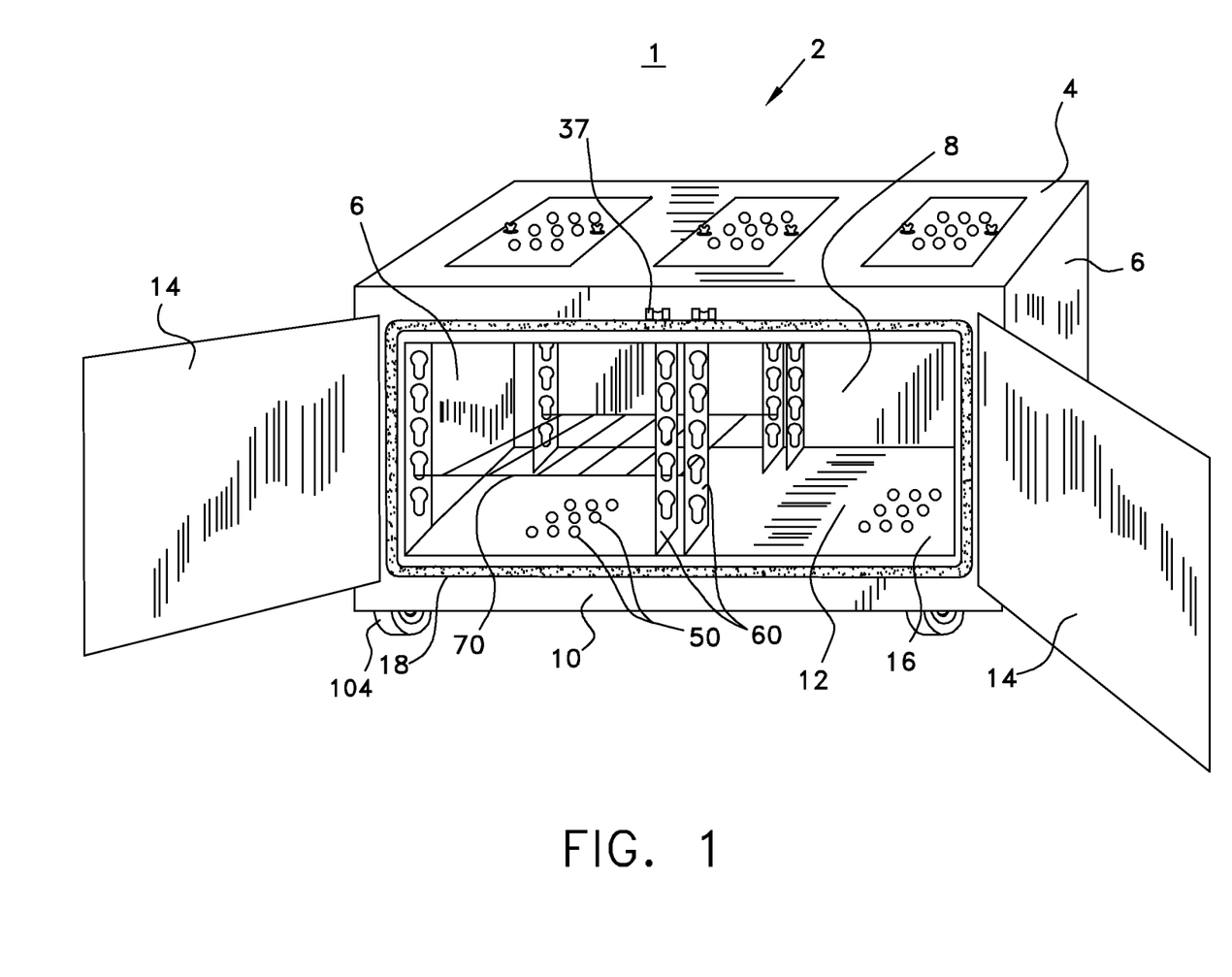
FIG. 1 is a front elevated isometric view of a mobile apparatus with its doors open.
Figure 2:
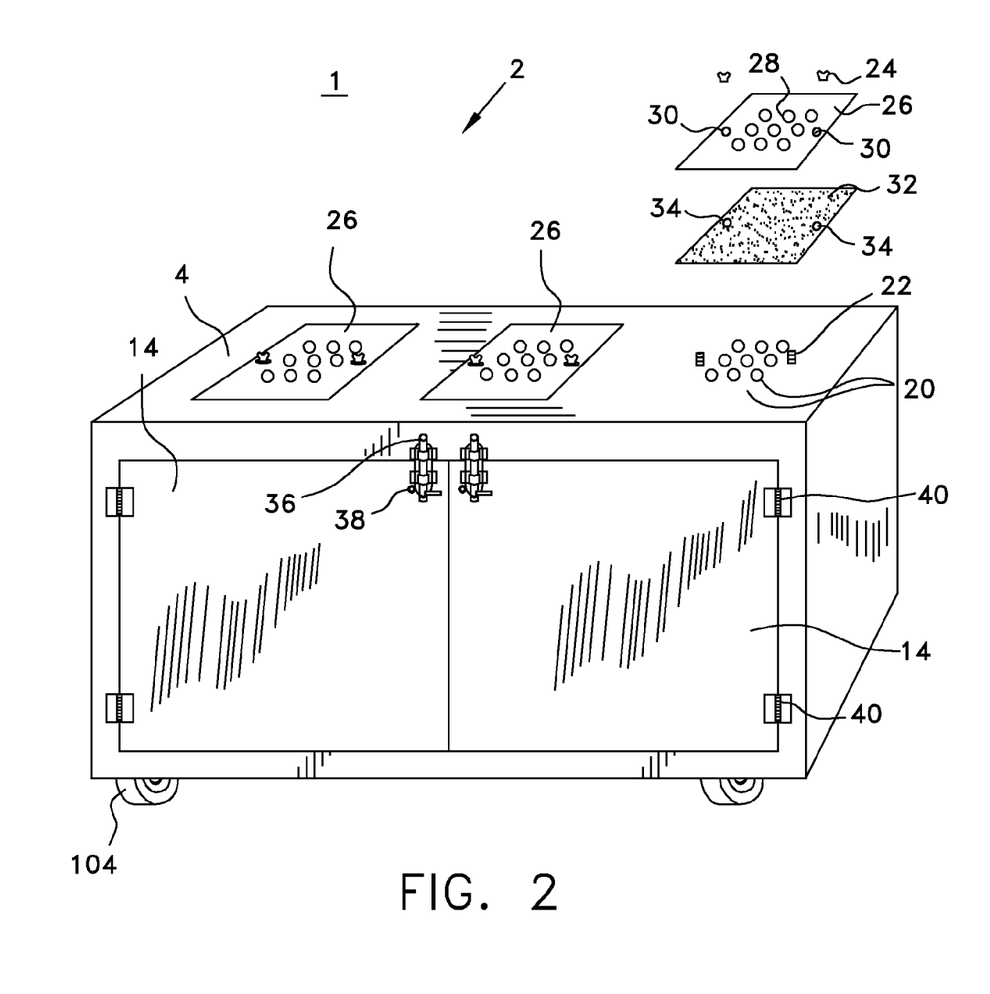
FIG. 2 is a front elevated isometric view of a mobile apparatus with its doors closed.

FIG. 1 is a front elevated isometric view of mobile apparatus 1 with its doors 14 open. FIG. 2 is a front elevated isometric view of mobile apparatus 1 with its doors 14 closed. The mobile apparatus 1 includes cabinet 2. Cabinet 2 comprises cabinet roof 4, cabinet sides 6, cabinet back 8, cabinet front 10, and cabinet floor 16. Cabinet front 10 contains cabinet front aperture 12, and at least one door 14 sized to cover cabinet front aperture 12. Gasket 18 is disposed around cabinet front aperture 12 and serves to seal doors 14 onto cabinet front 10 when doors 14 are closed. Thus, gasket 18 is sandwiched between doors 14 and cabinet front 10 when doors 14 are closed.

The interior of cabinet 2 contains a plurality of shelf supports 60. Shelf supports 60 are capable of supporting shelves 70 within cabinet 2. Shelves 70 serve to support surgical trays 80 inside cabinet 2.

Cabinet roof 4 contains a plurality of cabinet roof vents 20 arranged into groups. Each group of cabinet roof vents 20 is covered by filter 32 held in place by filter retainer 26. Each filter retainer 26 has a plurality of filter retainer vents 28 to allow passage of air through filter retainer 26, filter 32, and roof vents 20.

In the preferred embodiment, filter retainer 26 is removably attached to cabinet roof 4 by means of at least one threaded stud 22 rigidly attached to cabinet roof 4 and nut 24 being sized to mate with threaded stud 22. Filter 32 incorporates a filter bore 34 corresponding to each threaded stud 22 associated with a group of roof vents 20 covered by filter 32 and which is sized to admit threaded stud 22. Filter retainer 26 incorporates a filter retainer bore 30 corresponding to each threaded stud 22 associated with a group of roof vents 20 covered by filter retainer 26 and filter retainer bore 30 is sized to admit threaded stud 22.

Thus, in the preferred embodiment, filter 32 is held in position on cabinet roof 4 by means of at least one threaded stud 22 rigidly attached to cabinet roof 4 and extending through a corresponding filter bore 34, filter retainer bore 30, and a corresponding nut 24 threaded onto the threaded stud 22. In the preferred embodiment, filter 22 is substantially co-extended with filter retainer 26.

Cabinet floor 16 contains a plurality of cabinet floor vents 50 arranged into groups. As may also be observed in FIG. 7, each group of cabinet floor vents 50 is covered by filter 32 held in place by filter retainer 26. Each filter retainer 26 has a plurality of filter retainer vents 28 to allow passage of air through filter retainer 26, filter 32, and floor vents 50.

Figure 7:
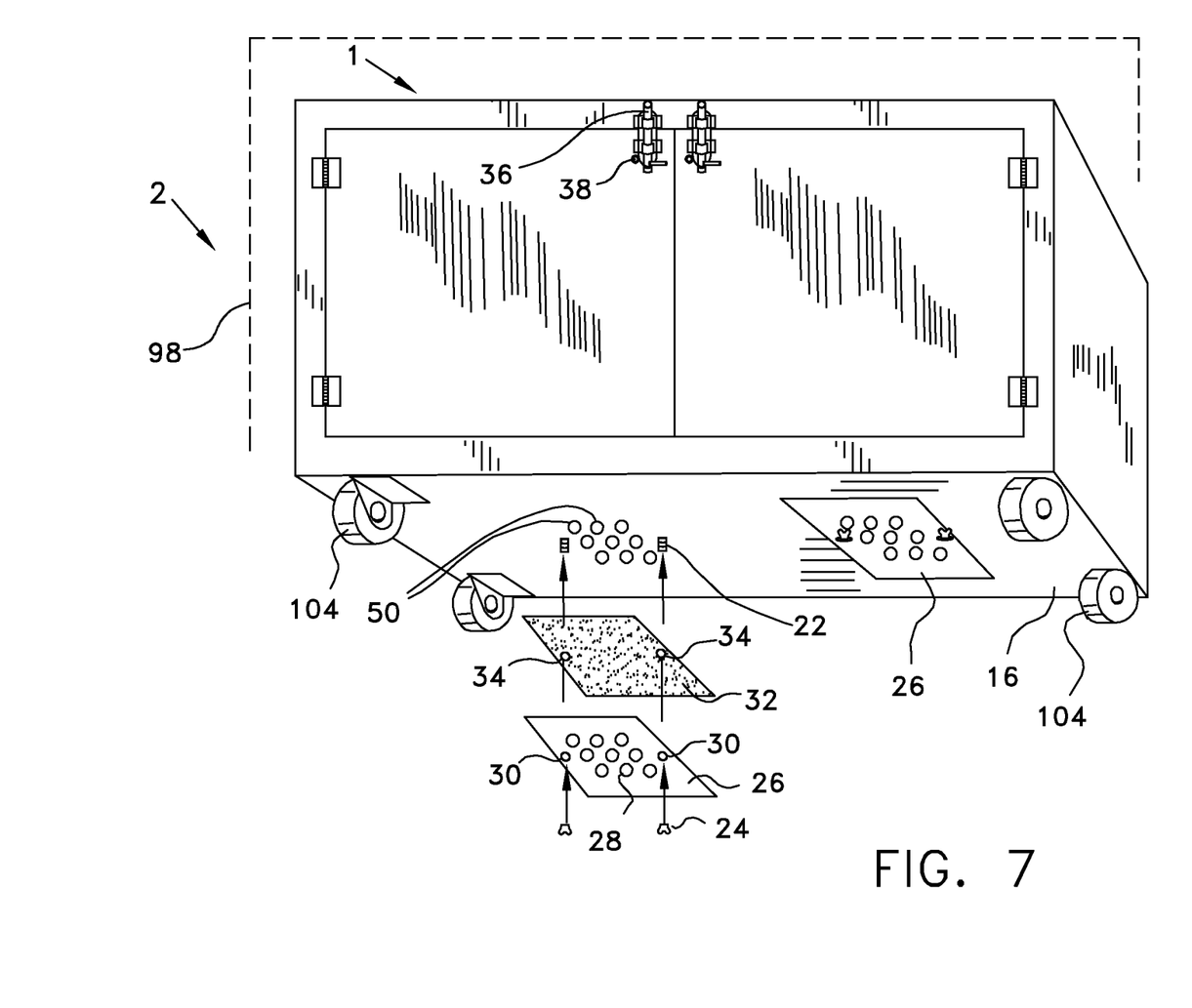
FIG. 7 is a front isometric view of a mobile apparatus with its doors closed, inside an autoclave, represented as a dashed line.

In the preferred embodiment, filter retainer 26 is removably attached to cabinet floor 16 by means of at least one threaded stud 22 rigidly attached to cabinet floor 16 and nut 24 being sized to mate with threaded stud 22. Filter 32 incorporates a filter bore 34 corresponding to each threaded stud 22 associated with a group of floor vents 50 covered by filter 32 and which is sized to admit threaded stud 22. Filter retainer 26 incorporates a filter retainer bore 30 corresponding to each threaded stud 22 associated with a group of floor vents 50 covered by filter retainer 26 and filter retainer bore 30 is sized to admit threaded stud 22.

Thus, in the preferred embodiment, filter 32 is held in position on cabinet floor 16 by means of at least one threaded stud 22 rigidly attached to cabinet floor 16 and extending through a corresponding filter bore 34, filter retainer bore 30, and a corresponding nut 24 threaded onto the threaded stud 22.

Door(s) 14 are hingedly attached to cabinet 2 by means of hinges 40. Door(s) 14 are secured in the closed position by means of door closure(s) 36 having door closure members 37. In the preferred embodiment, door closure 36 is a deadbolt type closure. Once surgical trays 80 are inserted into cabinet 2 and door(s) 14 are closed and secured in the closed position by door closure(s) 36, each door closure 36 is secured with a respective door closure safety 38. In the preferred embodiment, door closure safety 38 is an elongate member extending around door closure 36 and holding door closure 36 in the closed position, and requiring that door closure safety 38 be broken to allow door closure 36 to open.

Figure 3:
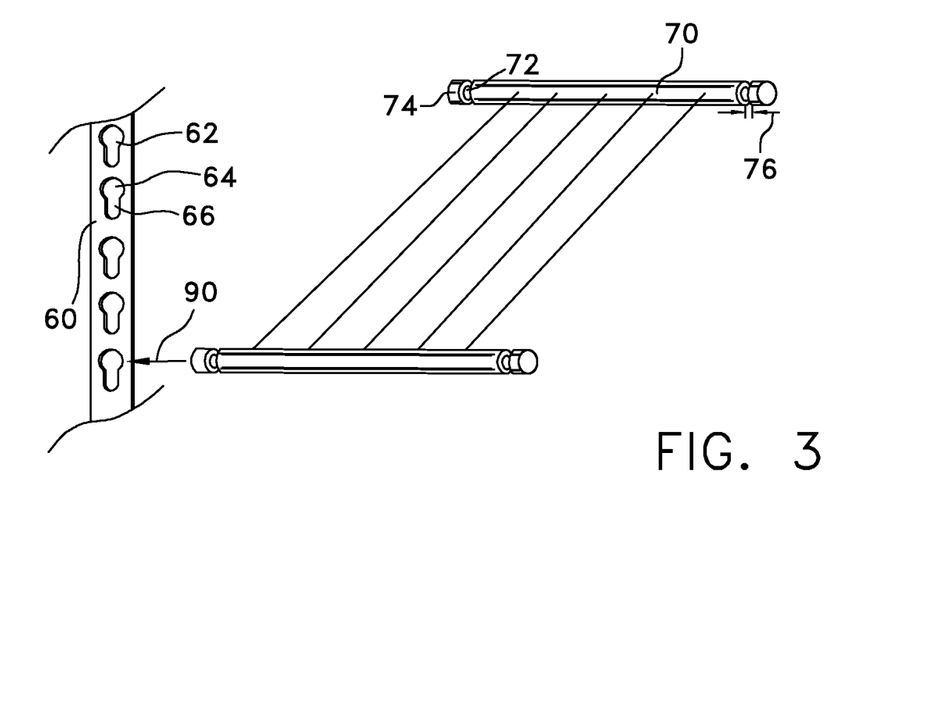
FIG. 3 is a front elevated isometric view of a shelf and a shelf support.

FIG. 3 is a front elevated isometric view of shelf 70 and a corresponding shelf support 60. Each shelf 70 is held within cabinet 2 by corresponding vertically-disposed shelf supports 60.

Each shelf support 60 comprises a plurality of shelf support apertures 62. In the preferred embodiment, each shelf support aperture 62 comprises an upper shelf support aperture major lobe 64 communicating with a lower shelf support aperture minor lobe 66. Each shelf 70 comprises a shelf cap 74 attached to a shelf neck 72.

A cross-sectional area of shelf cap 74 exceeds a cross-sectional area of shelf neck 72. Shelf support aperture major lobe 64 is sized to admit both shelf cap 74 and shelf neck 72, while shelf support aperture minor lobe 66 is sized to admit shelf neck 72 but not shelf cap 74.

Figure 4:
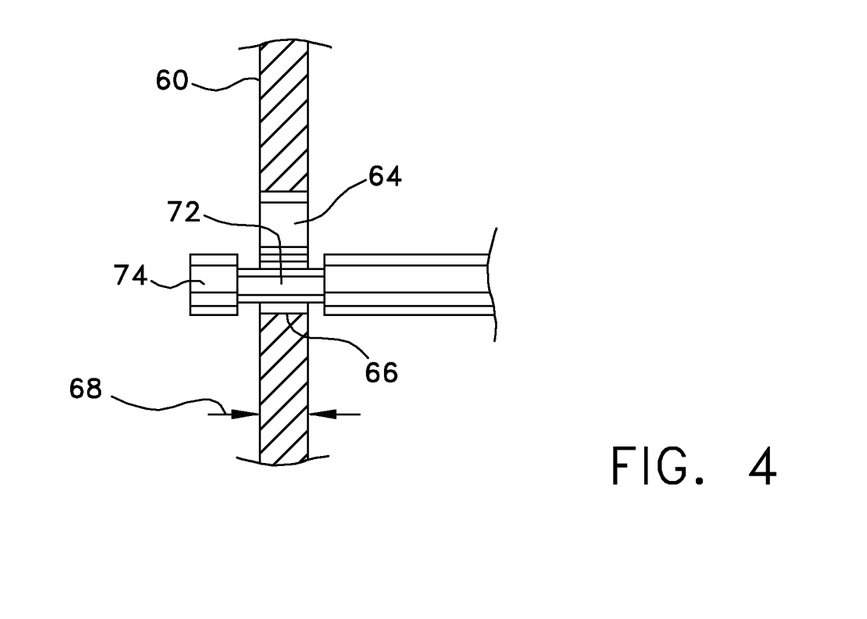
FIG. 4 is a side cross-sectional view of a shelf supported by a shelf support.

When mounting shelf 70 on shelf supports 60 within cabinet 2, each shelf cap 74 and shelf neck 72 pair is inserted into a corresponding shelf support aperture major lobe 64 as indicated by arrow 90 in FIG. 3 until shelf neck 72 aligns with shelf support aperture minor lobe 66, and then shelf neck 72 is slid downwards into shelf support aperture minor lobe 66 as depicted in FIG. 4, where the shelf 70 remains positioned under the influence of gravity.

It may be noted that shelf neck length 76 equals or exceeds shelf support thickness 68, which permits shelf neck 72 to fit into shelf support aperture minor lobe 66, as is shown in FIG. 4. FIG. 4 is a side cross-sectional view of shelf neck 72 resting within shelf support aperture minor lobe 66. Because shelf support aperture minor lobe 66 is sized to admit shelf neck 72 but not shelf cap 74, shelf neck 72 is prevented from sliding out of shelf support aperture minor lobe 66 by shelf cap 74, as is depicted in FIG. 4.

Figure 5:
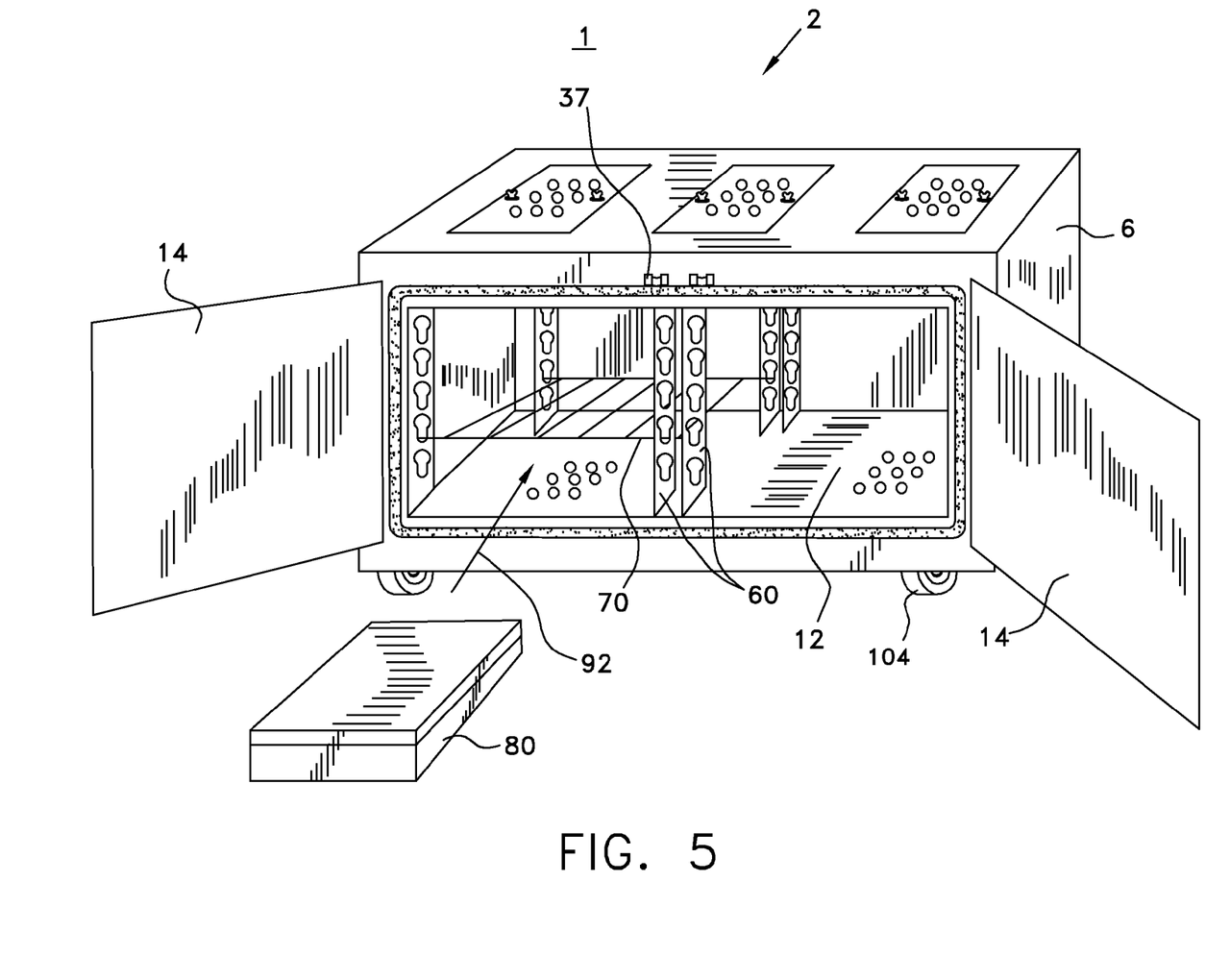
FIG. 5 is a front elevated isometric view of a mobile apparatus with its doors open and a surgical tray to be inserted into the cabinet.
Figure 6:
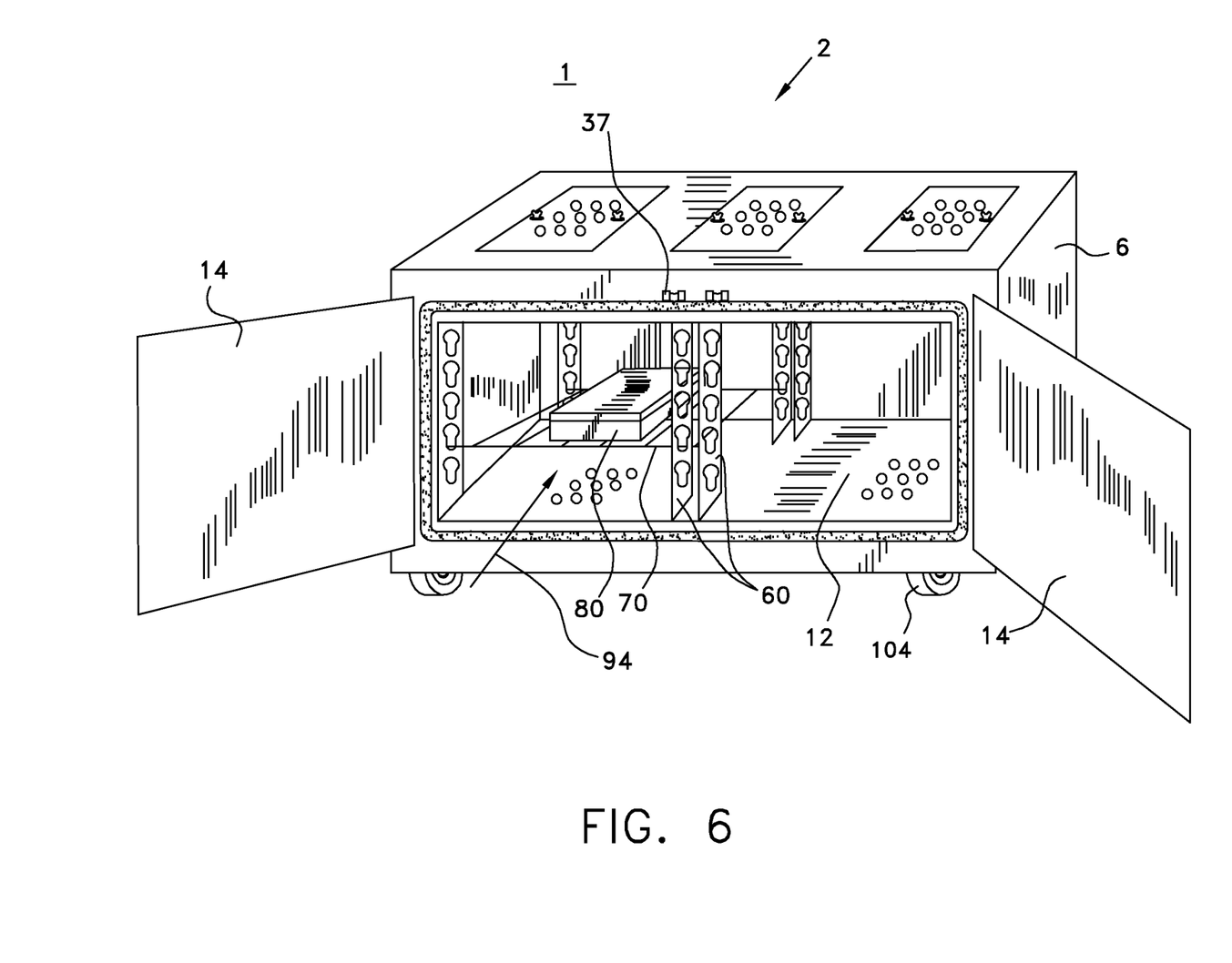
FIG. 6 is a front elevated isometric view of a mobile apparatus with its doors open and a surgical tray inside.

FIGS. 5 through 10 depict the instant method to sterilize surgical trays. FIG. 5 is a front elevated isometric view of mobile apparatus 1 with its doors 14 open and a surgical tray 80 to be inserted through cabinet front aperture 12 and onto shelf 70 in cabinet 2, as indicated by arrow 92. FIG. 6 is a front elevated isometric view of mobile apparatus 1 with its doors 14 open and surgical tray 80 inserted inside, as indicated by arrow 94, and resting upon shelf 70. In FIG. 5, door closure members 37 are shown coupled to the cabinet front 10.

FIG. 7 is a front isometric view of the mobile apparatus 1 with its doors 14 closed and inside autoclave 98, represented as a dashed line. A door closure safety 38 has been installed on each door closure 36 to prevent any subsequent un-intended opening of doors 14. Wheels 104 are rotatably mounted onto cabinet floor 16. Wheels 104 permit cabinet 2 to be easily wheeled into and out of autoclave 98 and into an operating room or other area as desired after the autoclaving step.

While doors 14 are closed during the autoclaving step depicted in FIG. 7, gasket 18 seals doors 14 against cabinet front 10 in order to maintain the sterilization integrity of the inside of cabinet 2 and its contents. After doors 14 have been closed, the only ambient air communication between the inside of cabinet 2 and the outside of cabinet 2 is filtered air via roof vents 20 and floor vents 50.

Figure 10:
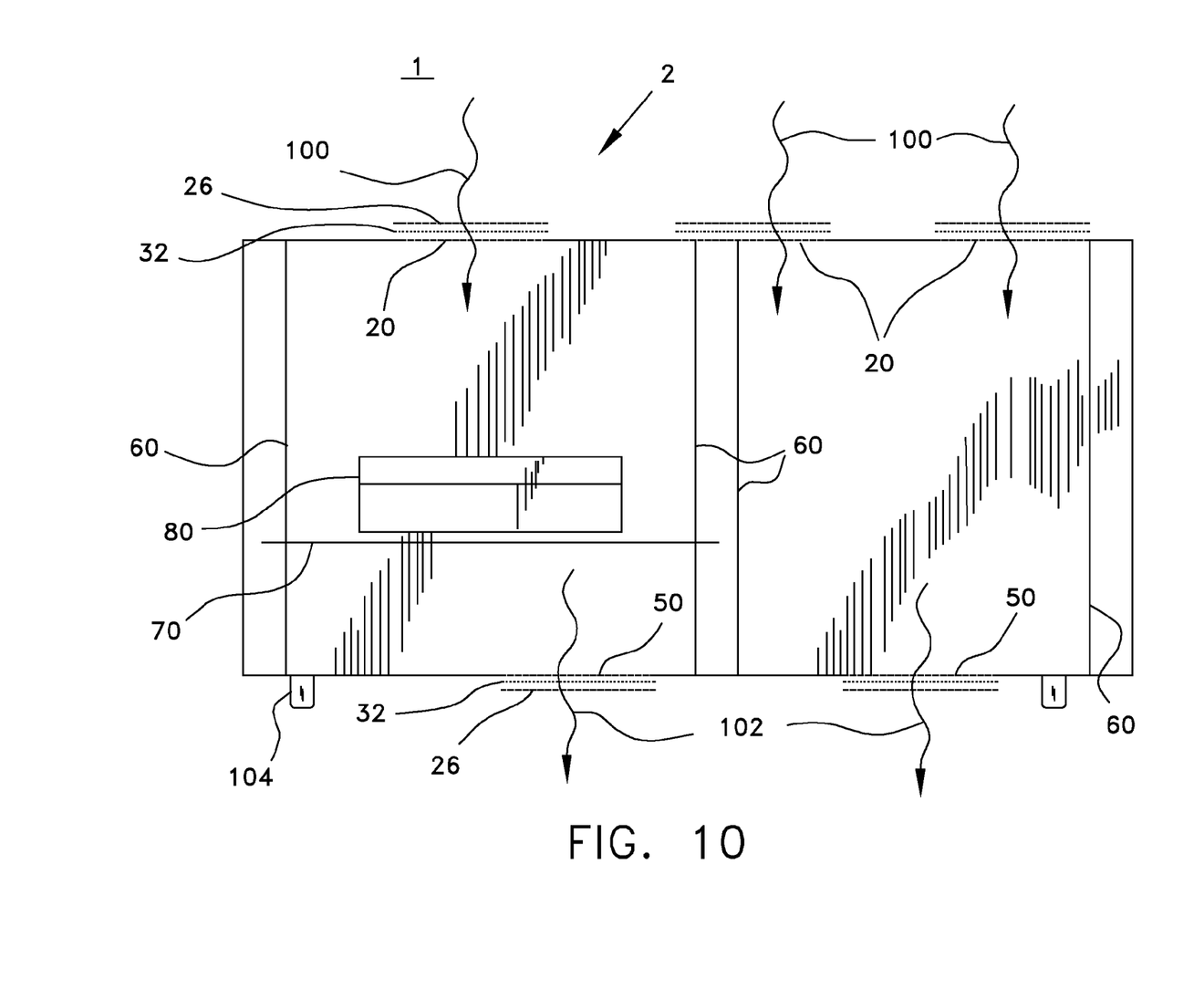
FIG. 10 is a front cross-sectional view of a mobile apparatus inside an autoclave, showing filtered airflow through the cabinet.

FIG. 10 is a front cross-sectional view of mobile apparatus 1 inside autoclave 98, showing air flow through cabinet 2. Due to the steam content of air within autoclave 98, heated steam and air flows through filter retainer 26, filter 32 and roof vents 20 into cabinet 2, as indicated by arrows 100 in FIG. 10. Within cabinet 2, the heated steam and air sterilize the interior of cabinet 2 and its contents and surgical tray(s) 80 and their contents. The surgical tray(s) 80 are on shelf 70 supported by shelf supports 60. Hot autoclave air, steam, and condensed water then exit cabinet 2 via floor vents 50, as indicate by arrows 102 in FIG. 10. The cabinet 2 includes wheels 104.

Figure 11:
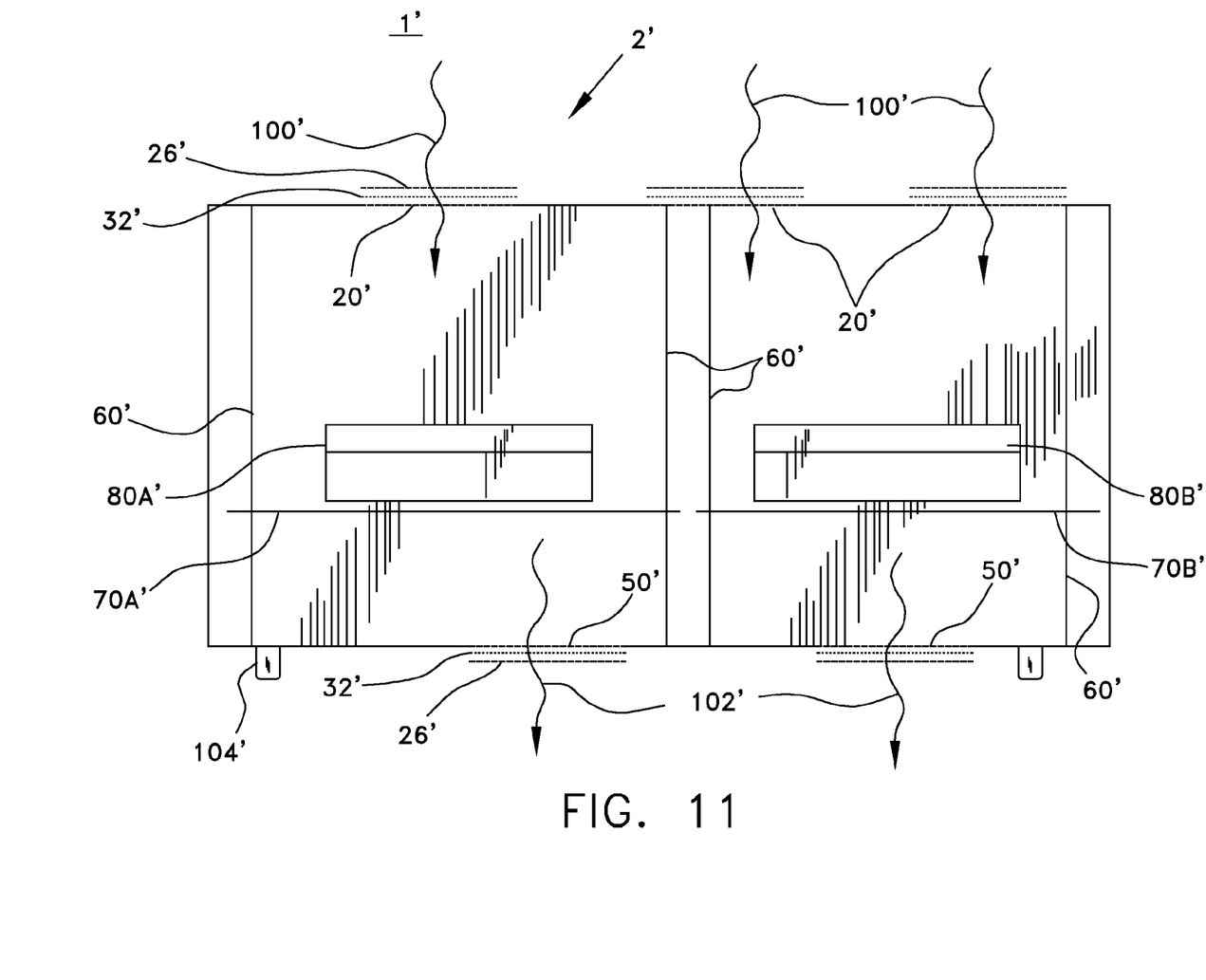
FIG. 11 is a front cross-sectional view of a mobile apparatus showing filtered airflow through the cabinet and with trays and shelves.

FIG. 11 is a front cross-sectional view of mobile apparatus 1' comprising a cabinet 2', showing air flow through cabinet 2'. Due to the steam content of air within the autoclave, heated steam and air flows through filter retainer 26', filter 32' and roof vents 20' into cabinet 2', as indicated by arrows 100' in FIG. 11. Within cabinet 2', the heated steam and air sterilize the interior of cabinet 2' and its contents and surgical tray(s) 80A' and 80B' and their contents. The surgical tray(s) 80A' and 80B' are on shelves 70A' and 70B' supported by shelf supports 60'. Hot autoclave air, steam, and condensed water then exit cabinet 2' via floor vents 50', as indicate by arrows 102' in FIG. 11. The cabinet 2' includes wheels 104'.

The instant method contemplates conventional autoclaving times and temperatures, in the order of 276 degrees Fahrenheit for thirty minutes. After the autoclaving step, cabinet 2 is removed for storage or use in the operating room. Door closure safeties 38 keep door closures 36 and doors 14 securely closed until cabinet 2 and its contents are ready for use in the operating room.

Figure 8:
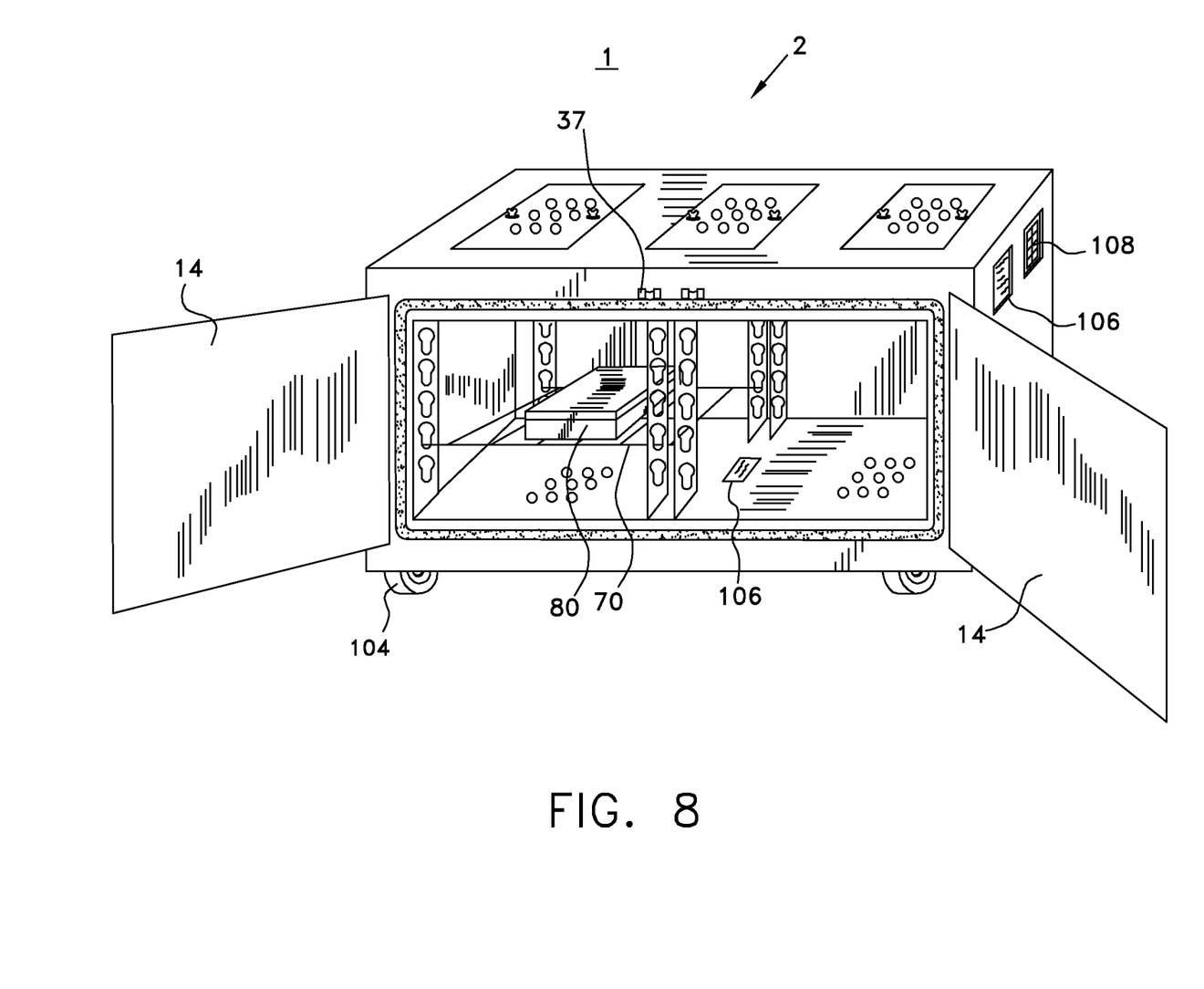
FIG. 8 is a front elevated isometric view of a mobile apparatus with its doors open and a surgical tray to be removed from the cabinet.

FIG. 8 is a front elevated isometric view of mobile apparatus 1 after autoclaving, ready to have its surgical tray(s) 80 used. Cabinet 2 has its doors 14 open and a surgical tray 80 about to be removed from the cabinet 2. In FIG. 8, door closure members 37 are shown coupled to the cabinet front 10.

Chemical indicators 106 are disposed on the side and inside of cabinet 2 as desired. In the preferred embodiment, five chemical indicators were disposed on and inside cabinet 2. Chemical indicators 106 indicate the sterilization status of cabinet 2. Because cabinet 2 remains sealed with doors 14 closed until ready for use in the operating room, it is not necessary to have one chemical indicator 106 in each surgical tray 80, as conventional practice dictates. The reduced number of chemical indicators 106 allowed by the instant apparatus and method provides significant cost savings compared to conventional surgical tray sterilization methods.

As may also be observed in FIG. 8, locator card 108 may be disposed on cabinet 2. Locator card 108 records the history of cabinet 2, e.g. the date and time that cabinet 2 has undergone autoclave sterilization.

Figure 9:
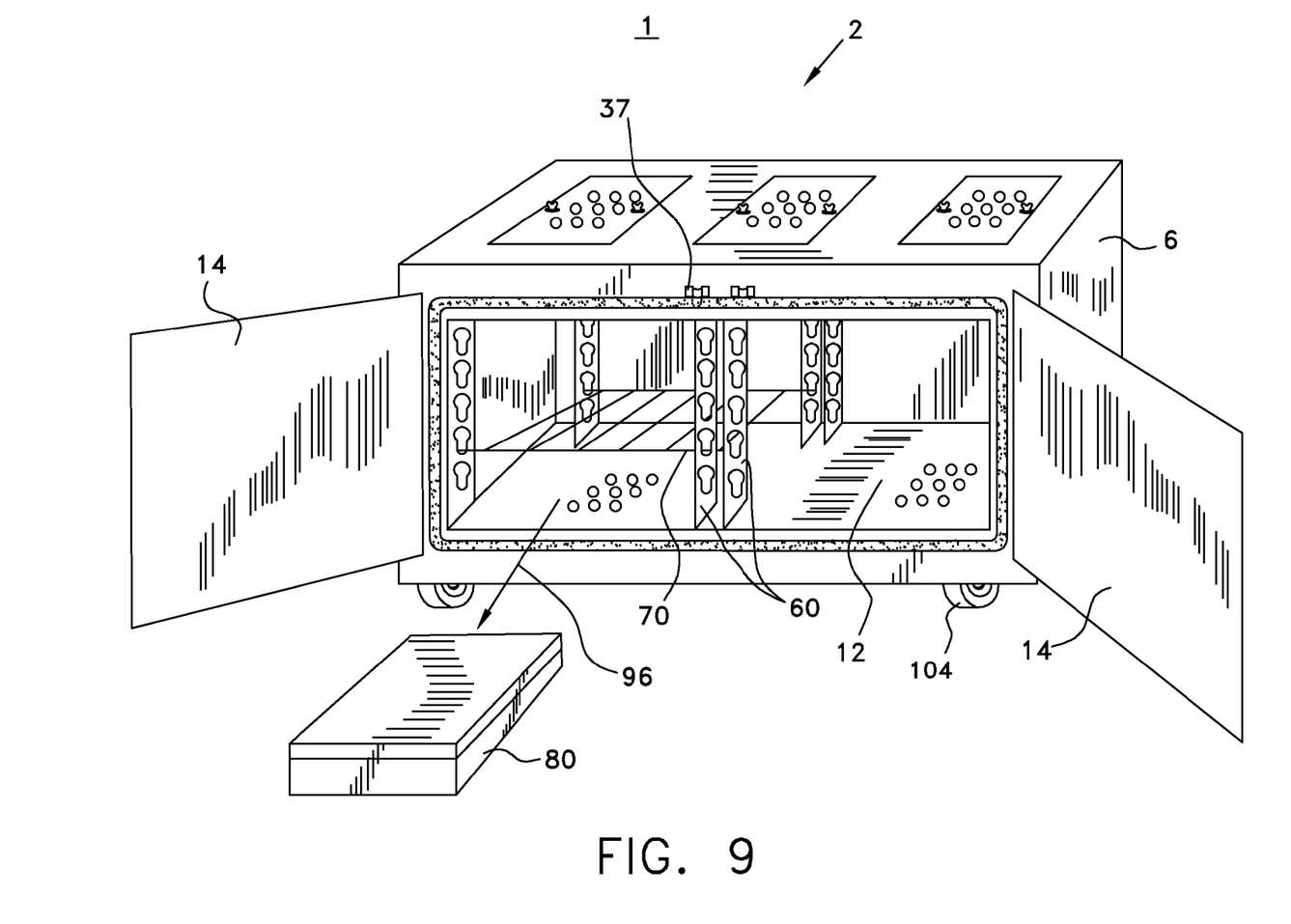
FIG. 9 is a front elevated isometric view of a mobile apparatus with its doors open and a surgical tray removed from the cabinet.

FIG. 9 is a front elevated isometric view of mobile apparatus 1 in use in an operating room, with its doors 14 open and a surgical tray 80 removed from cabinet 2, as indicated by arrow 96. In use, surgical tray 80 is opened conventionally and its sterilized contents (instruments, supplies, etc.) used conventionally. In FIG. 9, door closure members 37 are shown coupled to the cabinet front 10.

Thus, the instant method of sterilizing surgical trays comprises the steps of:

A. Washing a surgical tray 80;
B. Inserting the surgical tray 80 into a cabinet 2;
C. Sealing the doors 14 of the cabinet 2 by closing the doors 14;
D. Placing the mobile apparatus 1 within an autoclave 98;
E. Autoclaving the mobile apparatus 1 as desired to sterilize the cabinet 2 and its contents;
F. Allowing air and steam within the autoclave 98 to communicate with an interior of the cabinet 2 through a filter 32 and at least one vent;
G. Removing the mobile apparatus 1 from the autoclave 98;
H. Transporting the mobile apparatus 1 to an operating room or storage area;
I. Unsealing the cabinet 2 by opening its doors 14; and
J. Removing a surgical tray 80 from the cabinet 2.

The instant method may include the additional step of placing chemical indicators 106 inside the cabinet 2 before the autoclaving step and inspecting the chemical indicators 106 immediately before using the contents of the surgical trays 80.

The instant method may include the additional step of placing a chemical indicators 106 outside the cabinet 2 and inspecting the chemical indicators 106 immediately before using the contents of the surgical trays 80.

The instant method may include the additional step of placing a locator card 108 on the cabinet, inscribing indicia on the locator card 108 specifying that the cabinet has been autoclaved, and inspecting the locator card 108 before using the surgical trays 80.

The instant method may include the additional step of installing a door closure safety 38 on each door closure 36 prior to autoclaving, and removing the door closure safety 38 from each door closure 36 immediately prior to opening the cabinet doors 14 and removing a surgical tray 80 within the cabinet 2 for use.

The instant method may include the additional step of periodically replacing filters 32.

The instant method may include the additional step of periodically replacing the door gasket 18.

In the preferred embodiment, cabinet 2 and surgical tray 80 are manufactured of stainless steel, metal, synthetic, or other appropriate material. Filter 12 is a filter manufactured of paper, fabric, synthetic, or other appropriate material.

While the drawings depict threaded studs 22 extending away from an outer surface of cabinet 2; and filters 32, filter retainers 26 and nuts 24 outside cabinet 2, it is intended to fall within the scope of this disclosure that threaded studs 22, filters 32, filter retainers 26 and nuts 24 may be disposed within cabinet 2. For example, in this embodiment in the case of the filters 32 covering floor vents 50, threaded studs 22 extend upwards from cabinet floor 16, and nuts 24 hold retainer down on filter 32, thus holding filter 32 in contact with cabinet floor 16 over floor vents 50, as shown in FIG. 12.

Figure 12:
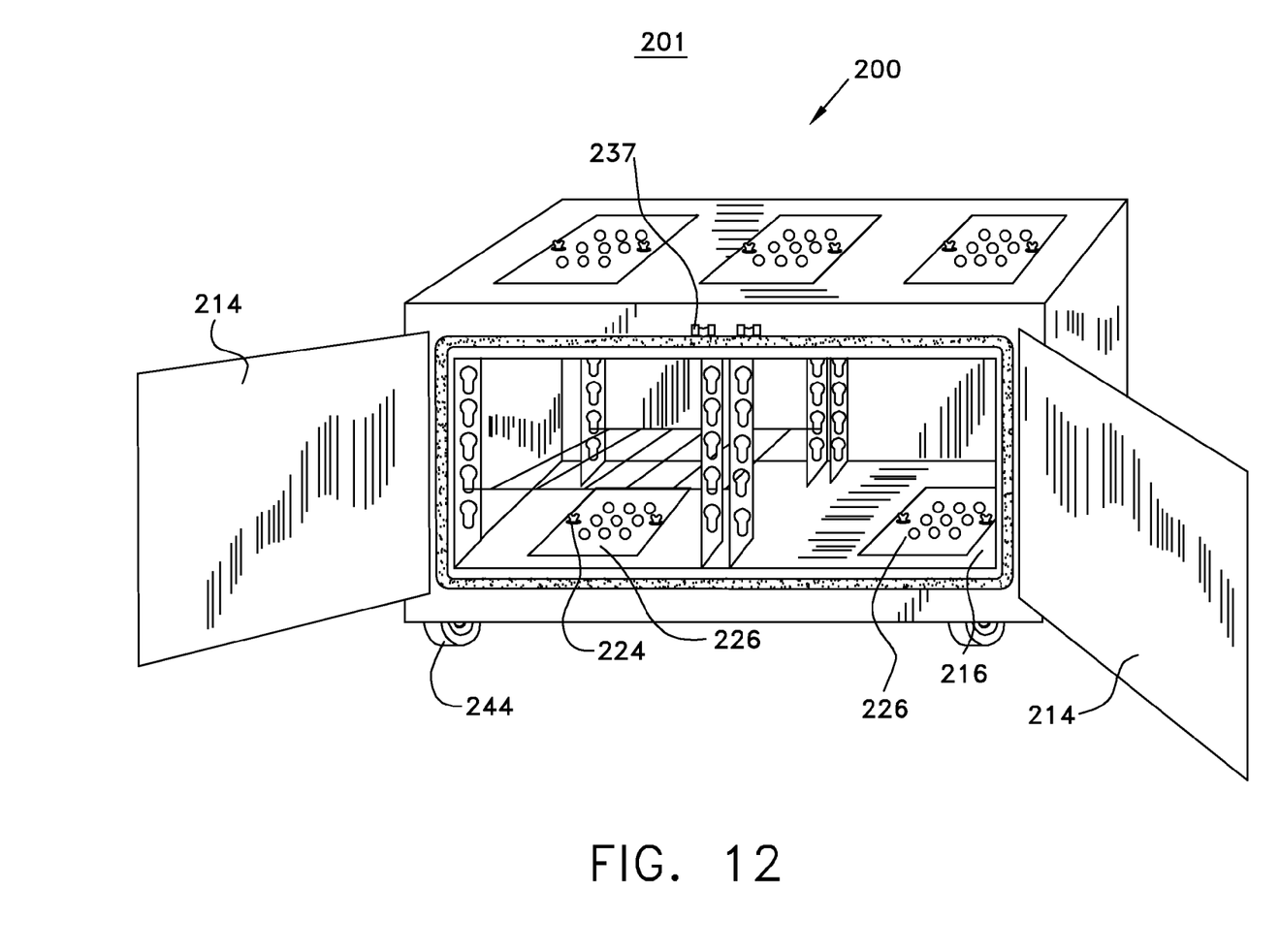
FIG. 12 is a front elevated isometric view of another mobile apparatus with its doors open.

FIG. 12 is a front elevated isometric view of another mobile apparatus 201 with its doors 214 open. The filter retainers 226 and nuts 224 of mobile apparatus 201 are shown over the floor vents in the cabinet floor 216. In FIG. 12, door closure members 237 are shown coupled to the cabinet front 210. The mobile apparatus 201 includes wheels 244.

Figures 13, 14:
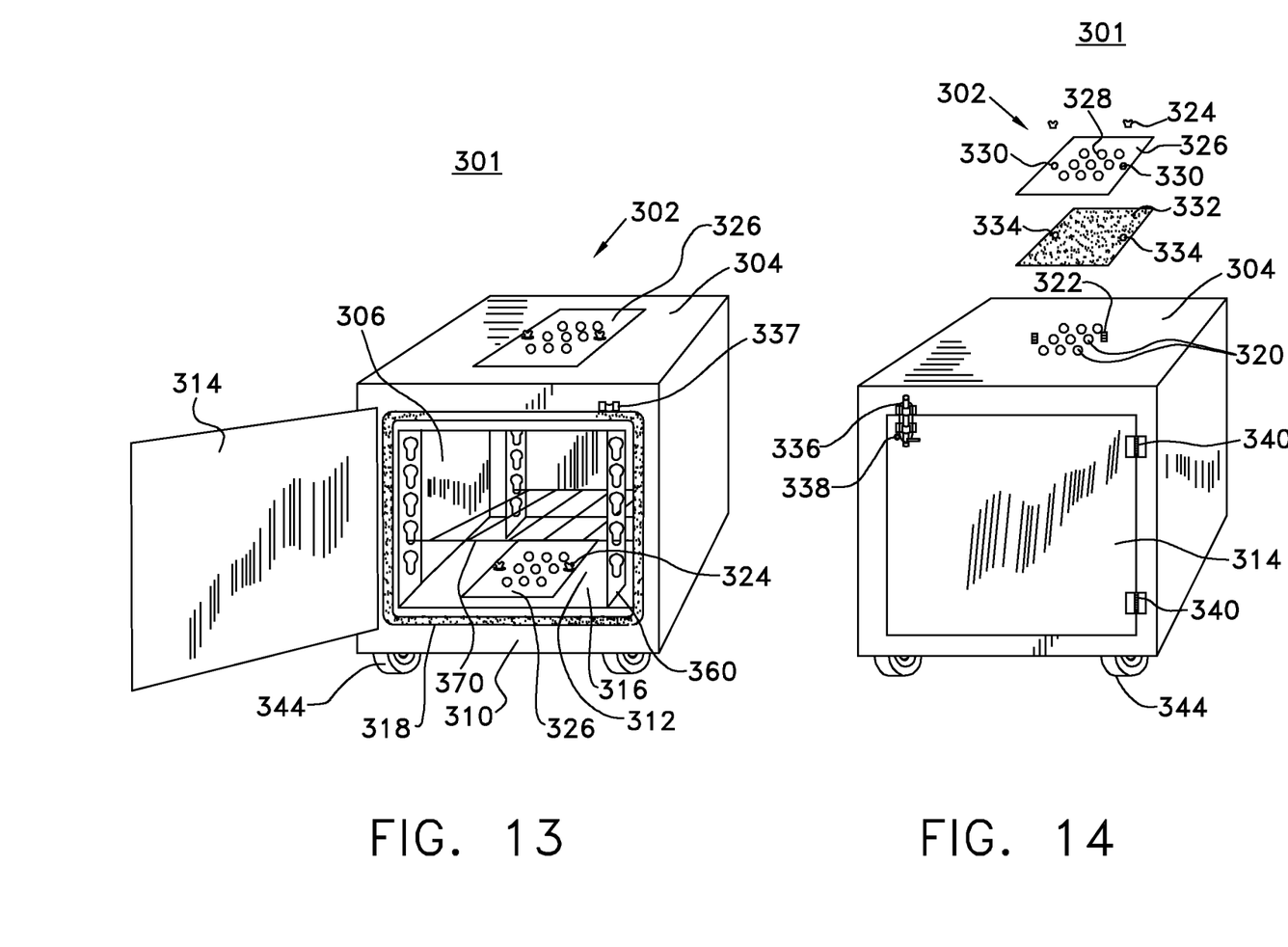
FIG. 13 is a front elevated isometric view of another mobile apparatus with its door open.
FIG. 14 is a front elevated isometric view of the mobile apparatus of FIG. 13 with its door closed.

FIG. 13 is a front elevated isometric view of another mobile apparatus 301 with its door 314 open according to exemplary embodiments of this invention. FIG. 14 is a front elevated isometric view of the mobile apparatus 301 of FIG. 13 with its door 314 closed. The mobile apparatus 301 includes a cabinet 302 and wheels 344. The cabinet 302 comprises a cabinet roof 304, cabinet sides 306, cabinet floor 316, cabinet front 310, at least one roof vent 320 in the cabinet roof 304, at least one floor vent (e.g., reference numeral 50 of FIG. 7) in the cabinet floor 316, a filter 332 covering the at least one roof vent 320, a filter 332 covering the at least one floor vent, a cabinet front aperture 312 in said cabinet front 310, and at least one door 314 hingedly attached to said cabinet front 310 via a plurality of hinges 340. The at least one door 314 covers the cabinet front aperture 312 when the door 314 is closed. Gasket 318 is disposed around cabinet front aperture 312 and serves to seal door 314 onto cabinet front 310 when door 314 is closed. The interior of cabinet 302 contains a plurality of shelf supports 360. Shelf supports 360 are capable of supporting shelve(s) 370 within cabinet 302.

In the preferred embodiment, filter retainer 326 is removably attached to cabinet floor 316 by means of at least one threaded stud rigidly attached to cabinet floor 316 and nut 324 being sized to mate with threaded stud. Filter 332 incorporates a filter bore 334 corresponding to each threaded stud 322 and which is sized to admit threaded stud 322. Filter retainer 326 incorporates a filter retainer bore 330 corresponding to each threaded stud 322 associated and which is sized to admit threaded stud 322. Each filter retainer 326 has a plurality of filter retainer vents 328 to allow passage of air through filter retainer 326, filter 332, and roof vents 320.

Door 314 is secured in the closed position by means of door closure 336 having door closure members 337. Once the surgical trays are inserted into cabinet 302 and door 314 is closed and secured in the closed position by door closure 336, door closure 336 is secured with a door closure safety 338.

While a preferred embodiment of the invention has been illustrated herein, it is to be understood that changes and variations may be made by those skilled in the art without departing from the spirit of the appending claims.

I claim:

1. A mobile apparatus for sterilizing surgical trays within an autoclave, the mobile apparatus comprising:
    a cabinet having a cabinet aperture and a plurality of vents, each of the plurality of vents being configured to be filtered;
    a first filter retainer associated with a first vent and a second filter retainer associated with a second vent, the first filter retainer configured to retain a first filter and the second filter retainer configured to retain a second filter, wherein the first vent and the first filter retainer are located on a roof of the cabinet and the second vent and the second filter retainer are located on a floor of the cabinet;
    at least one shelf coupled within the cabinet, the at least one shelf having an orientation parallel to said filters, and configured to support a plurality of surgical trays;
    at least one door hingedly attached to the cabinet and being configured to cover and seal the cabinet aperture when closed; and
    a plurality of wheels coupled to the floor of the cabinet, wherein the mobile apparatus is constructed to fit within the autoclave and wherein heated steam and air flows through the first filter into the cabinet to sterilize the interior of the cabinet and contents of the cabinet and steam, condensed water, and hot autoclave air exit the cabinet via the second filter.

2. The apparatus according to claim 1, further comprising a gasket configured to seal at least one door when the at least one door is closed.

3. The apparatus according to claim 1, further comprising at least one door closure affixed to the at least one door, at least one door closure being configured to secure the at least one door to the cabinet.

4. The apparatus according to claim 3, further comprising at least one door closure safety associated with the at least one door closure, the at least one door closure safety being configured to be broken in order to open the at least one door closure.

5. The apparatus according to claim 1, further comprising:
    shelf supports associated with interior sides of the cabinet wherein a height of the at least one shelf within the cabinet is adjustable.

6. The apparatus according to claim 1, wherein the first filter retainer and the second filter retainer are removable and the first filter and the second filter are replaceable.

7. The apparatus according to claim 1, further comprising at least one chemical indicator to be installed in the cabinet.

8. The apparatus according to claim 1, further comprising at least one locator card holder on the cabinet, the locator card holder to be configured to hold a card bearing indicia specifying whether the cabinet has been autoclaved.

9. The apparatus according to claim 1, the cabinet being made of stainless steel, metal, synthetic material, or combinations thereof.

10. The apparatus according to claim 1, the at least one door comprising two doors.

11. The apparatus according to claim 1, the at least one door comprising two doors.

12. The apparatus according to claim 1, the first vent and the second vent being formed in a roof of the cabinet.

13. The apparatus according to claim 12, further comprising a third vent formed in a roof of the cabinet wherein the third vent is configured to be filtered and covered with a filter retainer.

14. The apparatus according to claim 13, further comprising a fourth vent and a fifth vent formed in a floor of the cabinet wherein the fourth vent is configured to be filtered and covered with a filter retainer and the fifth vent is configured to be filtered and covered with a filter retainer.

* * * * *